(12) United States Patent
Shafirstein et al.

(10) Patent No.: US 11,344,742 B2
(45) Date of Patent: May 31, 2022

(54) SYSTEM AND METHOD FOR ADMINISTERING LIGHT THERAPY TO CURVED AND LARGE SURFACES

(71) Applicant: Health Research, Inc., Buffalo, NY (US)

(72) Inventors: Gal Shafirstein, Amherst, NY (US); Brian Wrazen, Cheektowaga, NY (US); David A. Bellnier, Buffalo, NY (US); Todd Demmy, Williamsville, NY (US)

(73) Assignee: Health Research, Inc., Buffalo, NY (US)

(*) Notice: Subject to any disclaimer, the term of this patent is extended or adjusted under 35 U.S.C. 154(b) by 188 days.

(21) Appl. No.: 15/746,685

(22) PCT Filed: Jul. 25, 2016

(86) PCT No.: PCT/US2016/043957
§ 371 (c)(1),
(2) Date: Jan. 22, 2018

(87) PCT Pub. No.: WO2017/015676
PCT Pub. Date: Jan. 26, 2017

(65) Prior Publication Data
US 2018/0207441 A1   Jul. 26, 2018

Related U.S. Application Data

(60) Provisional application No. 62/196,198, filed on Jul. 23, 2015.

(51) Int. Cl.
*A61N 5/06* (2006.01)
*A61B 18/22* (2006.01)
(Continued)

(52) U.S. Cl.
CPC .......... *A61N 5/0601* (2013.01); *A61N 5/062* (2013.01); *A61N 5/0616* (2013.01);
(Continued)

(58) Field of Classification Search
CPC .......... A61B 2018/00541; A61B 2018/00642; A61B 2018/00702; A61B 2018/00761;
(Continued)

(56) References Cited

U.S. PATENT DOCUMENTS 4,234,907 A * 11/1980 Daniel .................. D02G 3/441
362/556
4,761,047 A * 8/1988 Mori .................... A61N 5/0616
607/88

(Continued)

FOREIGN PATENT DOCUMENTS

EP   1072231 A1   1/2001
EP   1170034 A1   1/2002

*Primary Examiner* — Carl H Layno
*Assistant Examiner* — Michael J Lau
(74) *Attorney, Agent, or Firm* — Hodgson Russ LLP

(57) ABSTRACT

A system and method are disclosed that use a flexible guide (flap) and a scanning method to control the delivery of light dose to a treatment area. This approach overcomes the non-reliable delivery of light dose with a flap that conforms to the target area. Dosimetry control can be improved through the use of a computer controlled motor to move the laser fibers at known speed over the target tissue. In some embodiments, treatment time is reduced and illumination of large surfaces is achieved by using multiple fibers to deliver the light simultaneously.

22 Claims, 11 Drawing Sheets

(51) Int. Cl.
  *A61B 18/00* (2006.01)
  *A61B 18/20* (2006.01)
  *A61N 5/067* (2006.01)

(52) U.S. Cl.
  CPC ............. *A61B 2018/00541* (2013.01); *A61B 2018/00642* (2013.01); *A61B 2018/00702* (2013.01); *A61B 2018/00761* (2013.01); *A61B 2018/00779* (2013.01); *A61B 2018/2065* (2013.01); *A61B 2018/2255* (2013.01); *A61B 2018/2261* (2013.01); *A61N 5/067* (2021.08); *A61N 2005/063* (2013.01); *A61N 2005/0627* (2013.01); *A61N 2005/0628* (2013.01); *A61N 2005/0643* (2013.01)

(58) Field of Classification Search
  CPC .. A61B 2018/00779; A61B 2018/2065; A61B 2018/2255; A61B 2018/2261; A61N 2005/0627; A61N 2005/0628; A61N 2005/063; A61N 2005/0643; A61N 2005/067; A61N 5/0501; A61N 5/0616; A61N 5/062
  USPC .......................................................... 607/92
  See application file for complete search history.

(56) References Cited

U.S. PATENT DOCUMENTS

| | | | | |
|---|---|---|---|---|
| 5,212,749 A * | 5/1993 | Huggins | ............. | G02B 6/3644 385/62 |
| 5,568,964 A * | 10/1996 | Parker | ................... | D03D 15/00 362/556 |
| 5,766,234 A * | 6/1998 | Chen | ................ | A61B 17/00234 607/92 |
| 5,997,569 A * | 12/1999 | Chen | .................... | A61N 5/0601 607/88 |
| 6,138,046 A * | 10/2000 | Dalton | ................ | A61N 5/0601 356/300 |
| 6,443,978 B1 * | 9/2002 | Zharov | ................ | A61N 5/0616 607/91 |
| 7,168,862 B2 * | 1/2007 | Qi | ............................ | F21V 9/40 385/92 |
| 7,274,844 B2 * | 9/2007 | Walt | ..................... | A61B 5/6804 362/103 |
| 7,630,591 B2 * | 12/2009 | Allen | ................... | G01M 11/086 385/12 |
| 2002/0010500 A1 | 1/2002 | Chen | | |
| 2006/0111762 A1 * | 5/2006 | Sterenborg | ........... | A61N 5/0603 607/89 |
| 2006/0173514 A1 * | 8/2006 | Biel | ........................ | A61K 9/703 607/88 |
| 2007/0032845 A1 * | 2/2007 | Neuberger | ............. | A61N 5/062 607/89 |
| 2007/0208395 A1 | 9/2007 | Leclerc et al. | | |
| 2008/0082091 A1 | 4/2008 | Rubtsov et al. | | |
| 2009/0099459 A1 * | 4/2009 | Svanberg | ............... | A61N 5/0601 600/478 |
| 2009/0177094 A1 * | 7/2009 | Brown | ................. | A61B 5/0066 600/476 |
| 2011/0144503 A1 * | 6/2011 | Debreczeny | ......... | A61B 5/4523 600/476 |
| 2013/0144364 A1 | 6/2013 | Wagenaar Cacciola et al. | | |
| 2013/0295015 A1 * | 11/2013 | Deisseroth | ......... | A01K 67/0275 424/9.2 |
| 2014/0188035 A1 | 7/2014 | Ehrenreich et al. | | |
| 2015/0057724 A1 * | 2/2015 | Kuhn | ..................... | G06F 19/00 607/88 |

* cited by examiner

Flap Configuration

|  | AIR mW/cm² | WATER mW/cm² | 0.01% Lip. mW/cm² |
|---|---|---|---|
| 1 diffuser in middle | 6.10 | 4.52 | 3.76 |
| 2 diffusers in middle | 5.74 | 4.19 | 3.97 |
| 4 diffusers | 5.46 | 3.87 | 3.97 |
| 1 diff. in middle & Gold Foil | 8.29 | 6.32 | 6.46 |
| 2 diff. in middle & Gold Foil | 9.17 | 6.38 | 6.88 |
| 4 diffusers & Gold Foil | 9.30 | 6.73 | 7.16 |

Balloon Configuration

|  | AIR mW/cm² | WATER mW/cm² | 0.01% Lip. mW/cm² |
|---|---|---|---|
| 3 mm above surface | 3.14 | 2.76 | 3.12 |

Fig. 13

SYSTEM AND METHOD FOR ADMINISTERING LIGHT THERAPY TO CURVED AND LARGE SURFACES

CROSS-REFERENCE TO RELATED APPLICATIONS

This application claims priority to U.S. Provisional Application No. 62/196,198, filed on Jul. 23, 2015, now, the disclosure of which is incorporated herein by reference.

FIELD OF THE DISCLOSURE

The disclosure relates to administering light therapy to tissue.

BACKGROUND OF THE DISCLOSURE

Minimally-invasive light therapy comprises external beam illumination of the target tissue using, for example, a laser. The laser beam size determines the delivered light fluence or dose (J/cm$^2$). The target tissue must be illuminated at a prescribed light fluence rate and dose for an effective treatment. Typically, the light illumination is achieved by aiming the laser beam towards the target surface (treatment area). This may be practical when the treatment area is few centimeters in diameter (e.g., 0.5-3 cm) and its surface is relatively flat (as in non-melanoma skin cancer, or early stage oral lesions). In treating curved and larger lesions, the therapeutic illumination is accomplished by manually moving a laser beam over the treated area. The treating physician uses a spot source to treat flat large surfaces, or a balloon (diffused light) to treat large body cavities, such as the thoracic cavity. This technique of manually scanning results in uncontrolled light dose deposition, which in turns may lead to over or under treatment. Others have attempted to address this issue by using woven layers of optical fibers for dose delivery, utilizing motion tracking devices to track the dose administered by a physician, or robotic scans to administer the light dose. These solutions are expensive, cumbersome, and/or do not adequately control the delivery of the light dose.

BRIEF SUMMARY OF THE DISCLOSURE

A system and method are disclosed that use a flexible guide (flap) and a scanning method to control the delivery of light dose to a treatment area. This approach overcomes the non-reliable delivery of light dose with a flap that conforms to the target area. Dosimetry control can be improved through the use of a computer controlled motor to move the laser fibers at known speed over the target tissue. In some embodiments, treatment time is reduced and illumination of large surfaces is achieved by using multiple fibers to deliver the light simultaneously. In such embodiments, software can be used to synchronize fiber movements through the flap. Control of the light delivery is improved by using detection fibers and/or imaging, to monitor the light fluence rate and fluence distribution during treatment.

DESCRIPTION OF THE DRAWINGS

For a fuller understanding of the nature and objects of the disclosure, reference should be made to the following detailed description taken in conjunction with the accompanying drawings, in which:

FIG. 13 is a table showing the results of flap and balloon in comparison tests.

DETAILED DESCRIPTION OF THE DISCLOSURE

The present disclosure uses a template (flap) to guide treatment fibers with diffused working end (for emitting light) through channels that are at known distance from the target tissue. This approach allows:

(1) Improved light dosimetry to the target tissue. Since the distance from the treated surfaces is known and constant, the light dose can be adjusted by delivering more power through the laser fibers, by changing the scanning speed of the fibers, and/or by using multiple fibers.
(2) Light therapy delivered with multiple wavelengths.
(3) Incorporation of diagnosis.
(4) Use of thermal and non-thermal therapies, simultaneously or sequentially.
(5) Increased flexibility of the system compared to alternatives in the market or research.

In the present approach, a treatment fiber is either pulled or pushed through a channel within the flap, which parallel to the target lesion. The light dose is directly proportional to the rate of fiber movement, which can be controlled by a microprocessor. Well-defined light delivery can be accomplished by, for example, using multiple fibers in several channels or by moving one or more fibers from one channel to another.

Systems of the present disclosure advantageously allow: (1) Improved accuracy and repeatability of the light delivery to curved and large surfaces (such as, for example, the thoracic cavity); (2) improved control of light dose; (3)

treatment of specific regions while sparing others; (4) automation; (5) reduced treatment time; and (6) cost effective and simple treatment.

Figure 1:
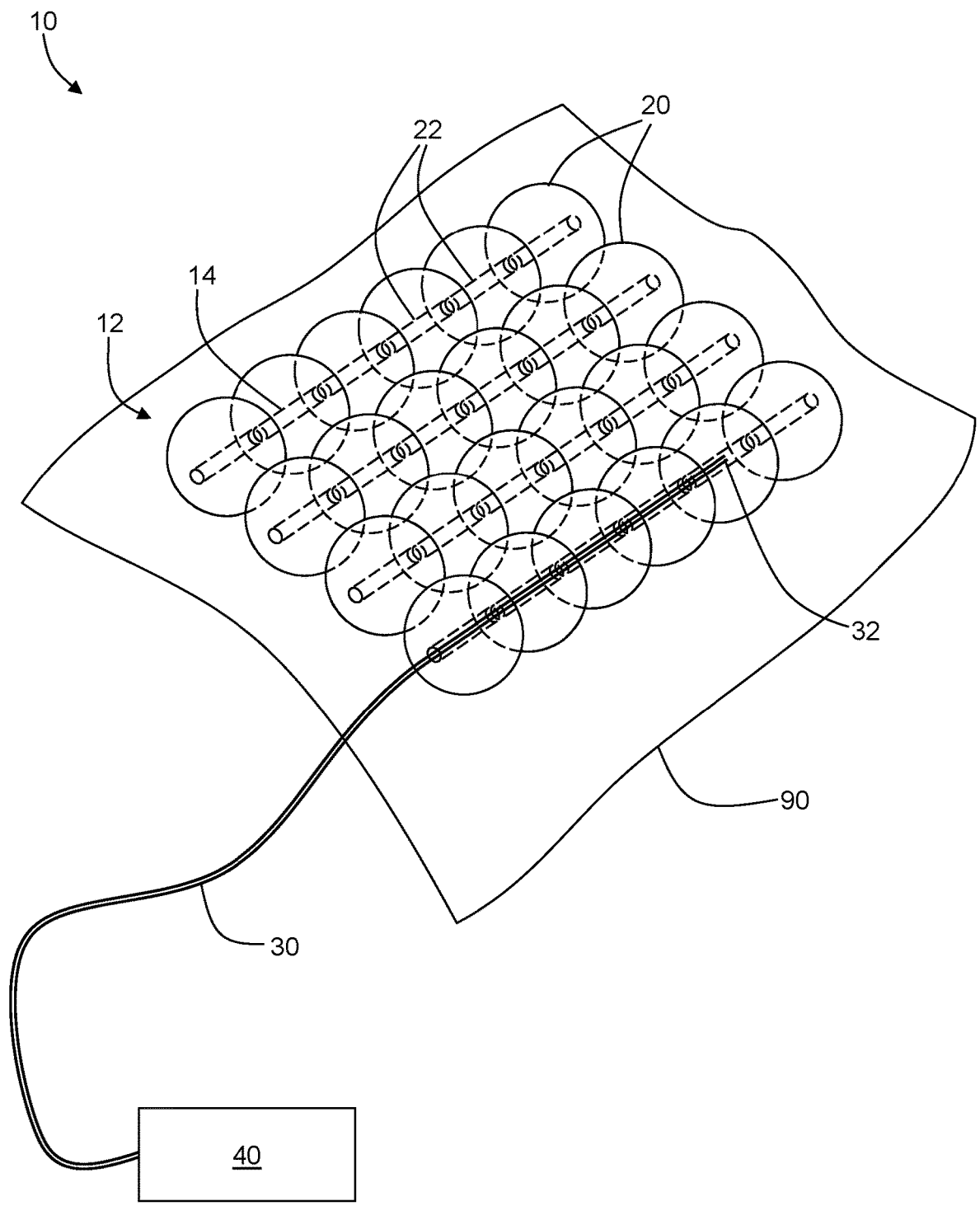
FIG. 1 is a diagram of a system according to an embodiment of the present disclosure.

With reference to FIG. 1, in one aspect, the present disclosure is embodied a system 10 for light therapy of a tissue surface 90 (although reference is made herein to treatment of a surface, it should be noted that such treatments may also penetrate to some depth of the tissue beneath the surface). The system 10 comprises a guide 12 that articulates to conform to the surface 90 being treated (the guide is sometimes referred to herein as a "flap"). The guide 12 includes one or more channels 14 having a length. The guide 12 is configured such that, when the guide 12 is conformed to the surface 90, the channels 14 are substantially a same distance from the surface 90 over the length of the channel 14.

In the exemplary embodiment depicted in FIG. 1, the guide 12 is made up of a plurality of spheres 20 arranged in a two-dimensional matrix. Each sphere 20 has a passage 22 disposed therethrough. The plurality of spheres 20 are disposed in one or more rows such that the passages 22 of each sphere 20 of a row are aligned to form a channel 14. When such a matrix is used, the guide 12 conforms to the surface such that all or substantially all (e.g., more than 80%, 90%, etc.) of the spheres 20 are in contact with the tissue. In this way, in an embodiment where the spheres 20 are 1 cm in diameter, the center of the channel 14 will be 0.5 cm from the tissue along the length of the channel 14.

Figure 3A:
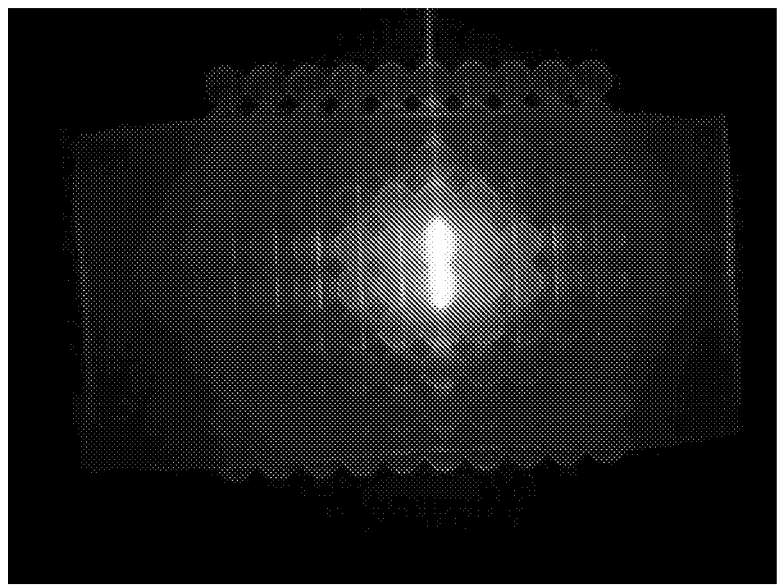
FIG. 3A shows light emitted from a treatment fiber and diffused through spheres of a guide.
Figure 3B:
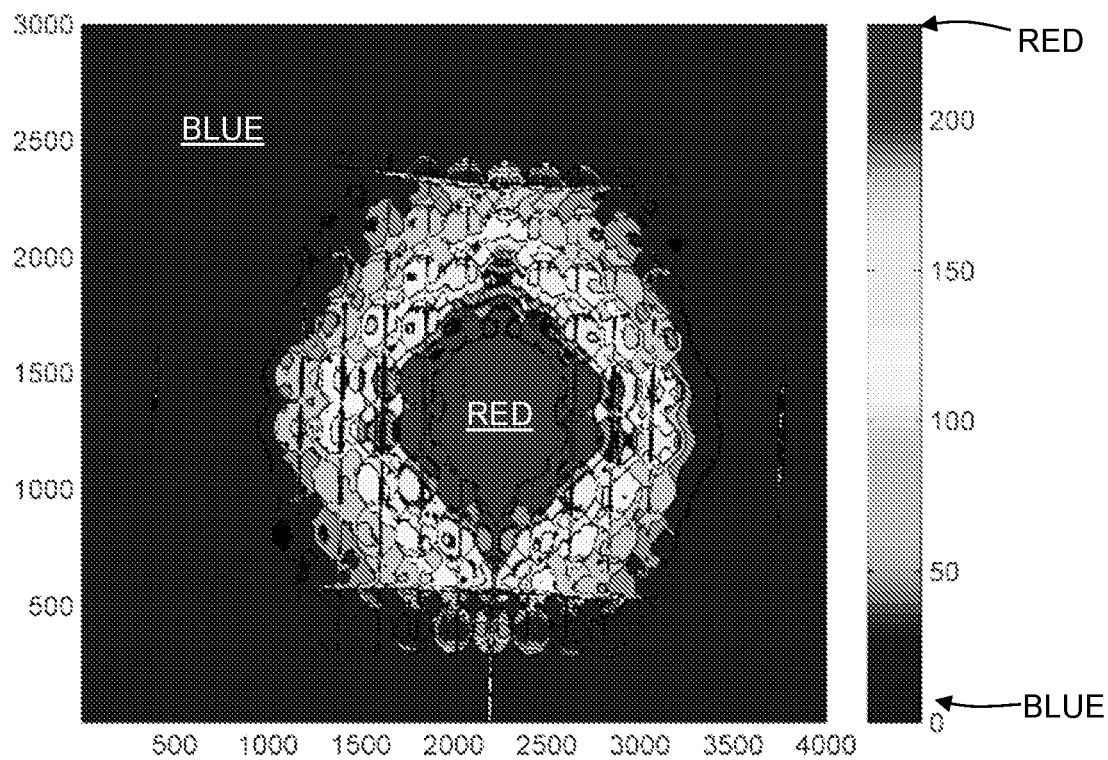
FIG. 3B depicts the intensity of light in FIG. 3A.
Figure 4A:
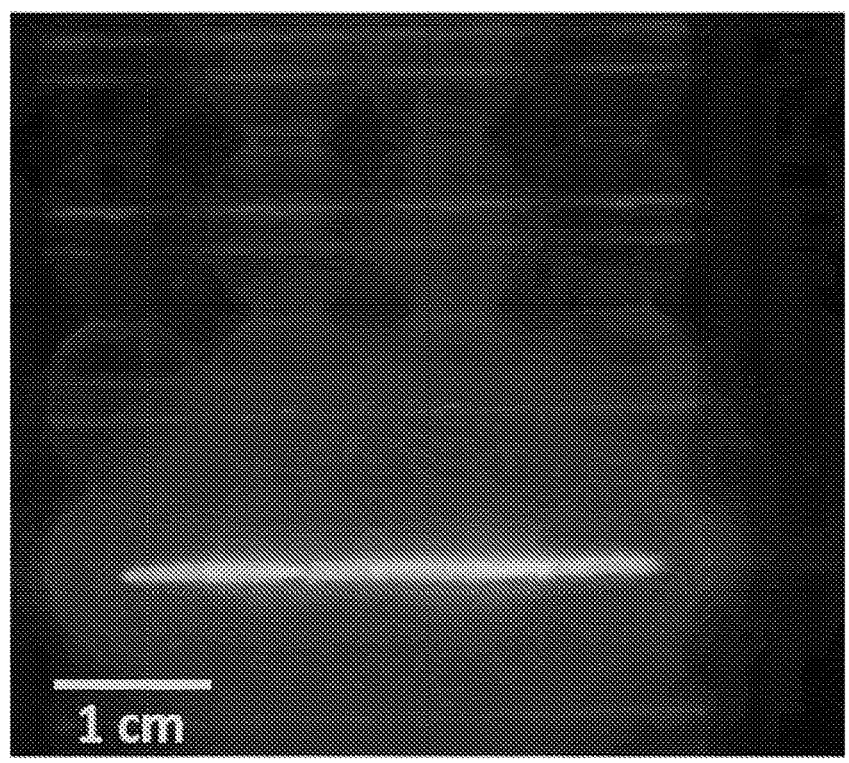
FIG. 4A shows light emitted from a flap that is fed with two 3 cm cylindrical diffusers emitting 630 nm at 400 mW/cm.
Figure 4B:
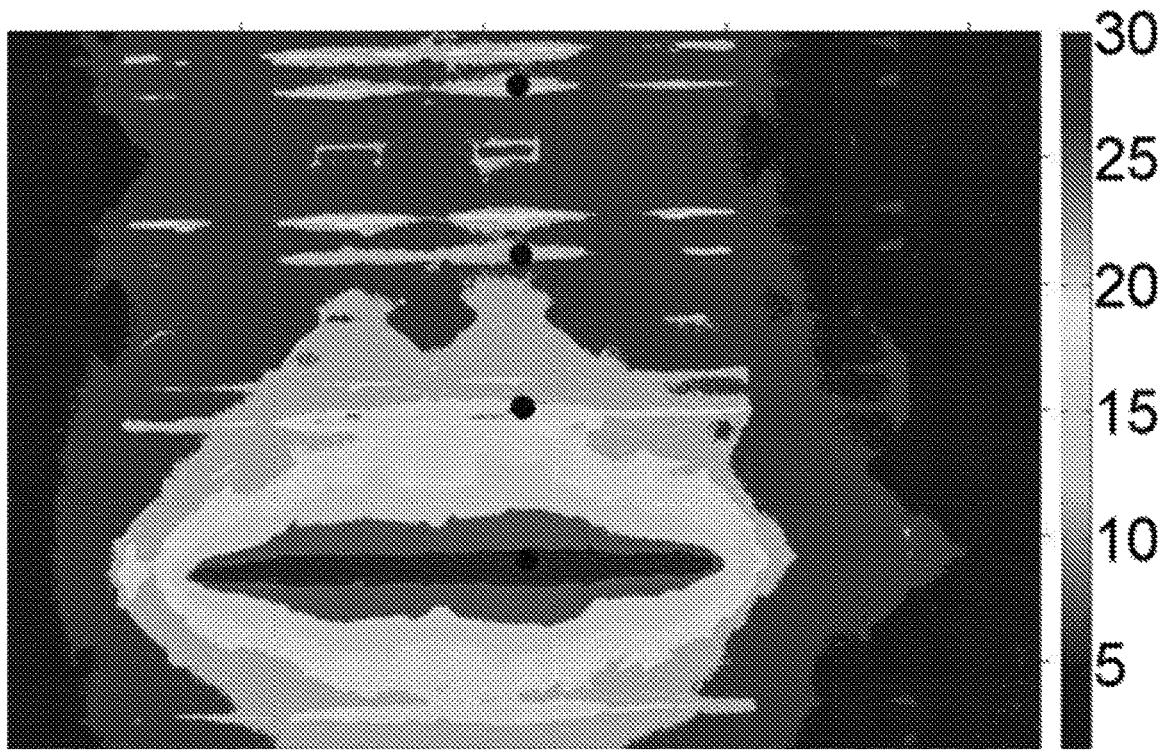
FIG. 4B depicts the intensity of light in FIG. 4A.

The spheres 20 may be transparent or translucent. The spheres 20 may be made from, for example, silicone rubber, plastic, or other materials. In some embodiments, the spheres 20 may have some treatment—such as, for example, a surface treatment, embedded material, etc.—configured to diffuse light. In this way, light from a small light source within the channel, will be diffused to some extent. Such diffusion can be advantageous in delivering light therapy. FIGS. 3A and 3B show light diffusion from a fiber located in the channel of an exemplary sphere-based guide. It can be seen that the light emanating from a small source has been diffused by the spheres. In some embodiments, the system 10 may comprise a diffusing sheet configured to diffuse the light from the guide 12. Such a diffusing sheet may be disposed between the guide 12 and the tissue surface 90 to further diffuse the light. In some embodiments, a diffusing sheet is placed on the opposite side of the guide 12 as the tissue. In this way, light can be reflected back to the tissue. In other embodiments, one or more sheets may be placed such that tissue regions are protected from exposure to light. In such embodiments, a sheet can be used in the form of a mask. Various combinations of sheets can be used. Sheet material can be selected based on the desired function (e.g., light blocking, light diffusing, light reflecting, etc.)

Figure 2A:
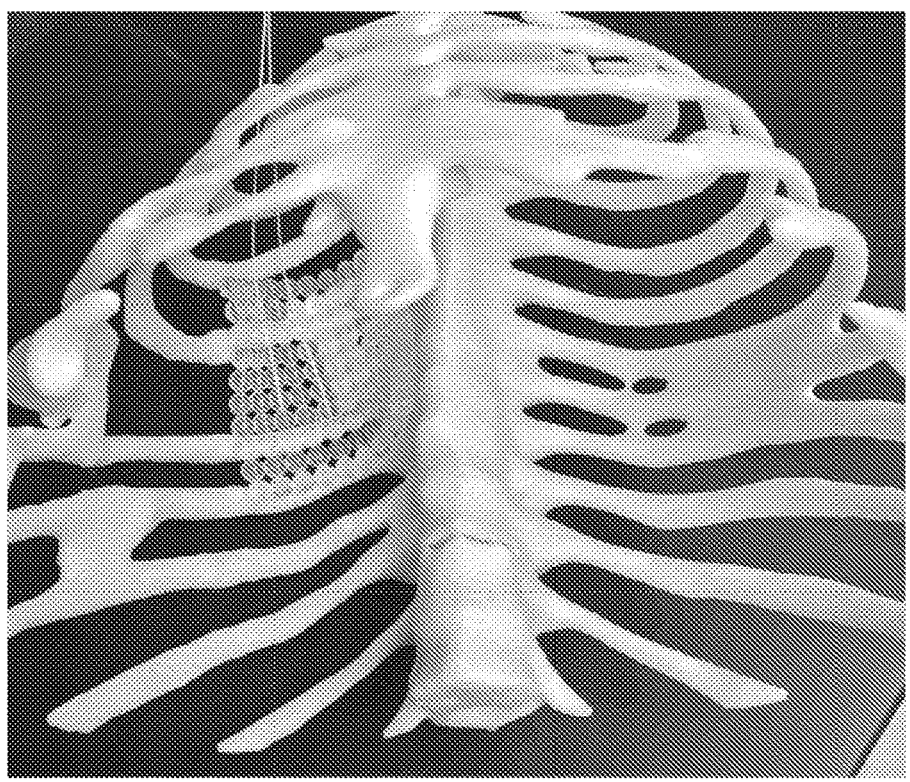
FIG. 2A shows a guide and two treatment fibers disposed in a model of a chest cavity.
Figure 2B:
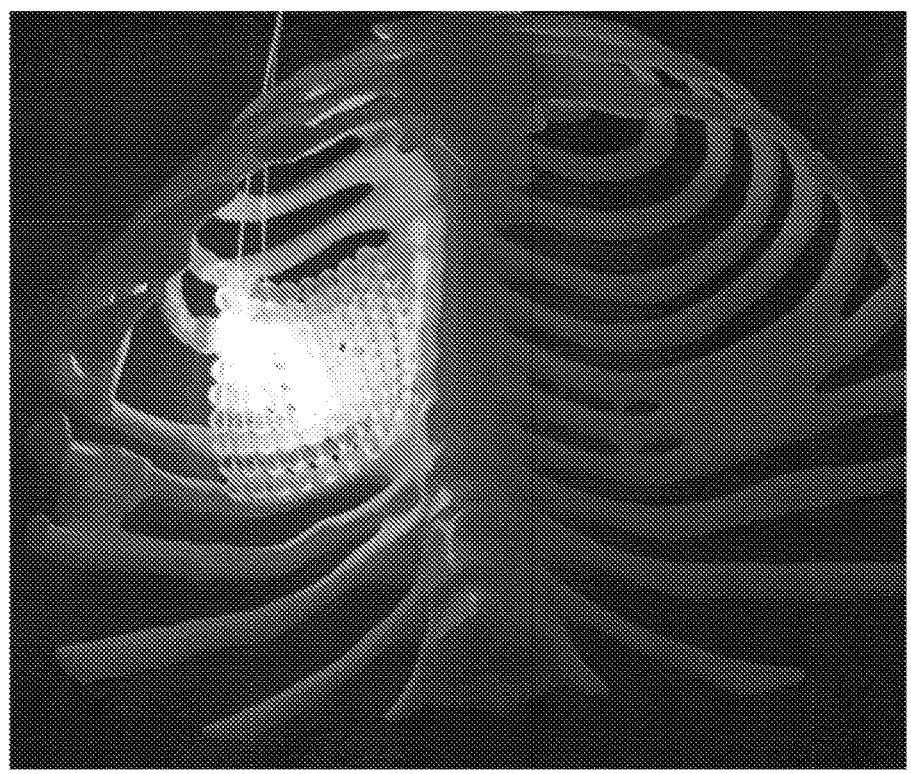
FIG. 2B shows the guide of FIG. 2A with light emitted from the treatment fibers.

The system 10 further comprises a treatment fiber 30 having a working end 32 for emitting light. The working fiber 30 is, for example, a light-transmitting fiber with a ball end where light is emitted at the working end 32. The treatment fiber 30 is configured to be disposed in the channel 14. For example, the channel 14 may have a diameter of 0.5 mm, and the treatment fiber 30 may have a diameter of 0.98 mm over at least a length of the treatment fiber 30 which is configured to be disposed in the channel 14. In some embodiments, more than one treatment fiber 30 is used. For example, 2, 3, 4, or more treatment fibers 30 may be used simultaneously, each treatment fiber 30 being disposed in another of the channels 14 of guide 12. FIG. 2A show an exemplary mat placed in a model rib cage of a human and having two treatment fibers disposed within two of the channels. In FIG. 2B, the working ends of the fiber are shown emitting light.

A therapeutic light source 40 is in light-transmitting communication with the working end 32 of the treatment fiber 30. Where more than one fiber 30 is used, each fiber 30 may be connected to a separate source 40 or two or more of the fibers 30 may be connected with a single source 40. The source 40 may be, for example, a laser. In other embodiments, the source 40 is a broadband light source which may be unfiltered or filtered to transmit one or more wavelengths of light. It should be noted that a reference to one wavelength of light should be interpreted in view of known practical limits of light transmission, and should be interpreted to mean a narrow band of wavelengths surrounding the single wavelength.

Through the use of a guide 12 with channels 14, the working end 32 of the treatment fiber 30 may be moved back and forth within the channel 14 during therapy. In this way, the surface 90 beneath and around a channel 14 will be exposed to light emanating from the working end 32 within that channel 14, and light can be more uniform because movement of the fiber 30 is constrained to a single degree of freedom—i.e., back and forth within the channel 14. The doseage is provided according to the speed of movement of the working end 32 (i.e., the time of exposure of a particular portion of the surface) and the intensity of the light.

In some embodiments, the light source 40 is controlled by a microcontroller such that the intensity can be varied. The light may be varied in accordance with the location of the working end 32 within the channel 14. In some embodiments, the light is varied according to doseage measured by sensors on the surface. The microcontroller may be programmed to vary the light for any other reasons that will be apparent in light of the present disclosure.

In some embodiments, the system 10 further comprises an armature or other mover for moving the working end 32 within the channel 14. In this way, the fiber 30 may be moved by the mover and not be manual operation by a physician or other user. The mover may also be controlled by a microcontroller (which may be the same microcontroller as described above or a different microcontroller). The mover may alter the speed at which the fibers are moved and/or the total duration of treatment time to accomplish the desired therapeutic light dose. In this way, the system 10 may be automated such that once placed into position, control by a physician is not necessary for its continued operation.

In some embodiments, measurement of the dosage is achieved using a measurement fiber (dosimetry fiber) which can be disposed in the same channel 14 as the treatment fiber 30 or a different channel 14. More than one dosimetry fiber can be used and the dosimetry fibers can be moved or can be motionless within the channels. Information measured through the use of such fibers can be provided as feedback to the microcontroller such that the light intensity, motion of the treatment fibers 30, and/or treatment time can be altered accordingly.

Figure 14:
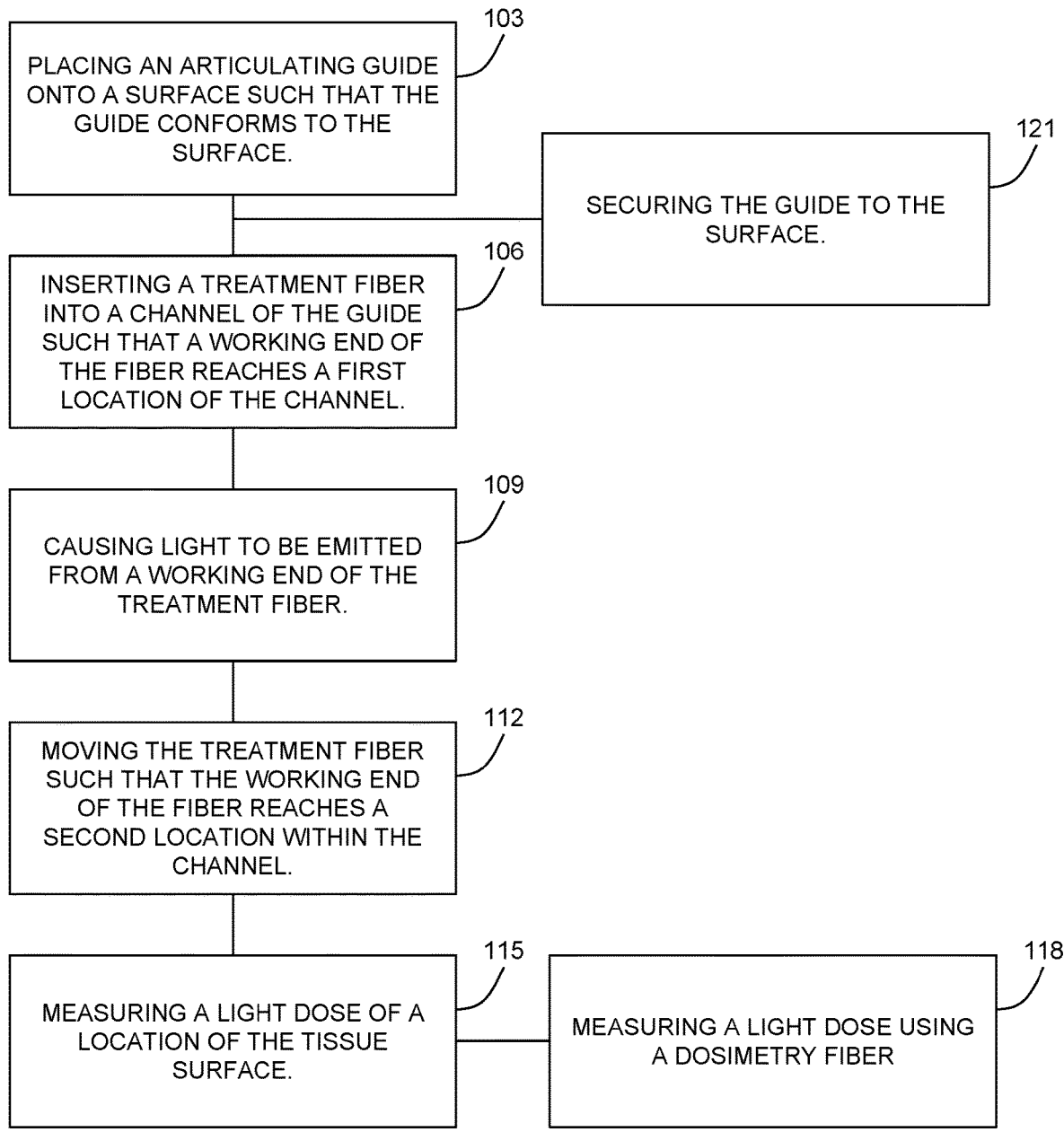
FIG. 14 is a chart depicting a method according to an embodiment of the present disclosure.

In another aspect of the present disclosure (for example, shown in FIG. 14), a method 100 for light therapy of a tissue is provided. The method 100 comprises placing 103 an articulating guide onto the surface such that the guide conforms to the surface. The guide may be configured as in any of the embodiments described above. In some embodiments, the method 100 includes securing 121 the guide onto the surface. For example, the guide may be sutured to the tissue.

A treatment fiber is inserted 106 into a channel of the guide until a working end of the treatment fiber reaches a first location of the channel. The method 100 comprises causing 109 light to be emitted from the working end of the fiber. For example, a light source connected to the fiber may be energized such that light is transmitted through the fiber (through the axial length of the fiber) and emitted from the working end. The fiber is moved 112 such that the working end of the fiber reaches a second location within the channel.

In some embodiments, more than one treatment fibers are inserted 106 into channels of the guide. For example, two treatment fibers may be inserted 106, each fiber being inserted into a separate channel of the guide. Each of the treatment fibers may be moved 112 together with the other treatment fibers (i.e., coordinated) or one or more of the fibers may be moved 112 independently of the other fiber(s).

The inserted 106 fiber may be moved back and forth within the channel from the first location to the second location (and or other locations) until a sufficient light dose has been received by the surface. As such, the method 100 may comprise measuring 115 a light dose of a location of the tissue surface. Such measurement may be made by, for example, sensors on the surface, a dosimetry fiber inserted 118 into a channel of the guide, or in other ways known for making such dosimetry measurements.

The fiber may be moved until a desired dosage (e.g., a predetermined dosage) is reached for the tissue at each of one or more locations of the surface. The fiber may then be removed and/or the light emission is ceased.

EXEMPLARY EMBODIMENTS

Figure 5:
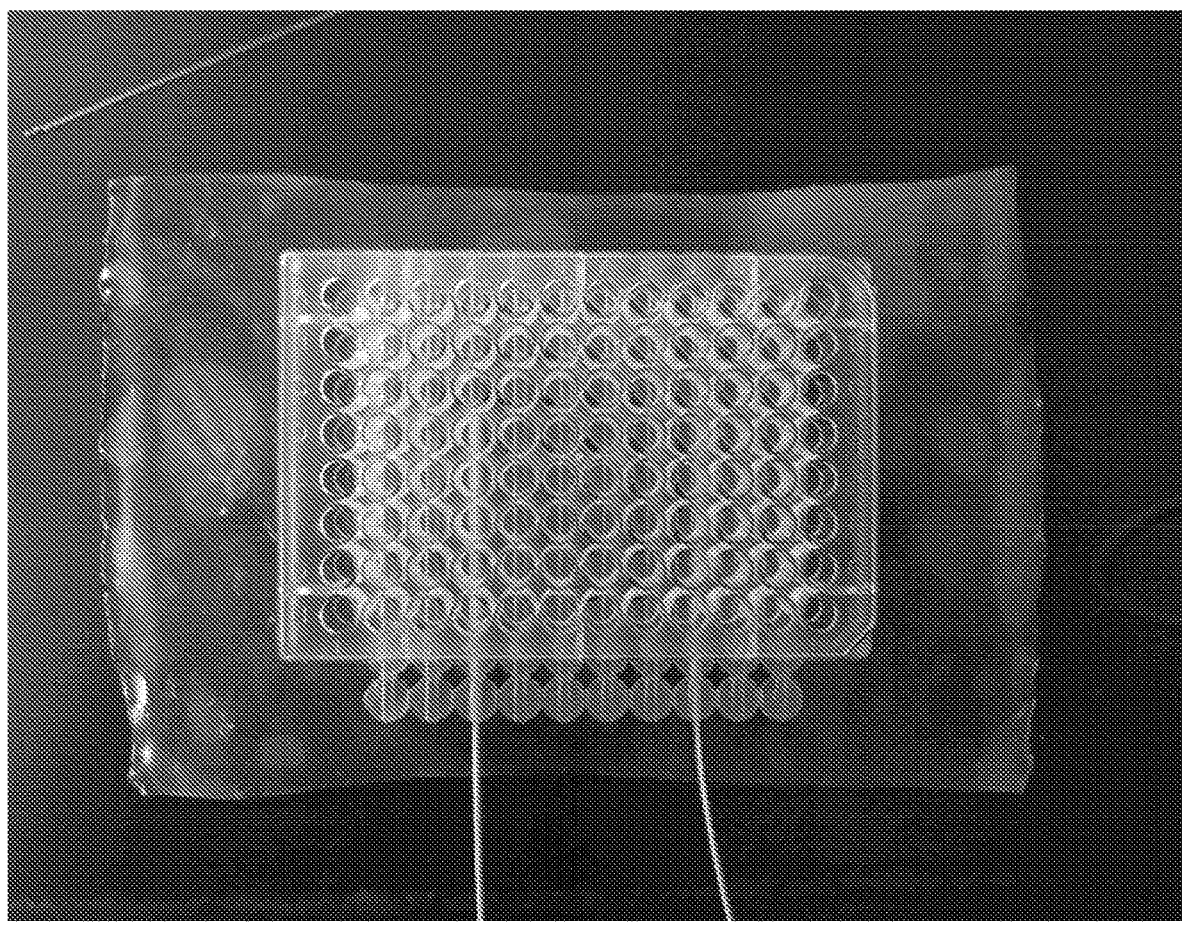
FIG. 5 depicts a test configuration wherein a flap is disposed between two layers of phantom and a 96 well plate is disposed on a side of one of the phantom layers opposite the side of the flap.
Figure 6:
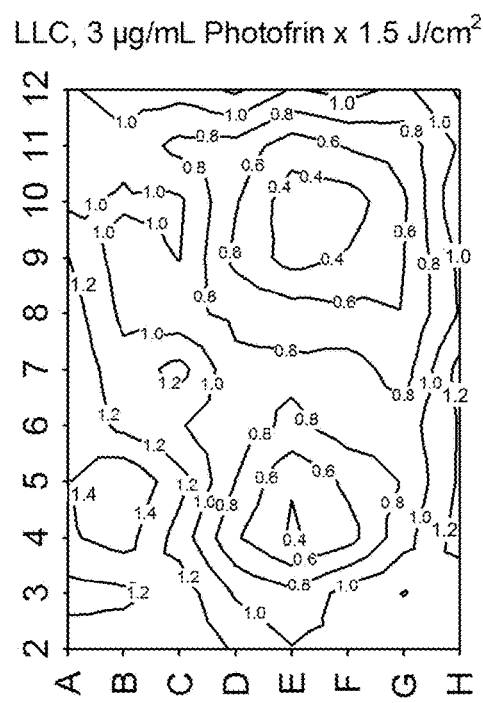
FIG. 6 are graphs showing test results of the configuration of FIG. 5.
Figure 6:
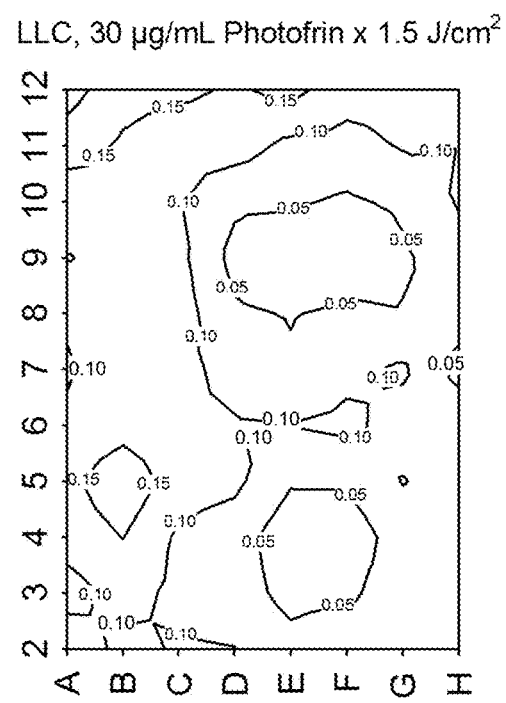
Figure 7:
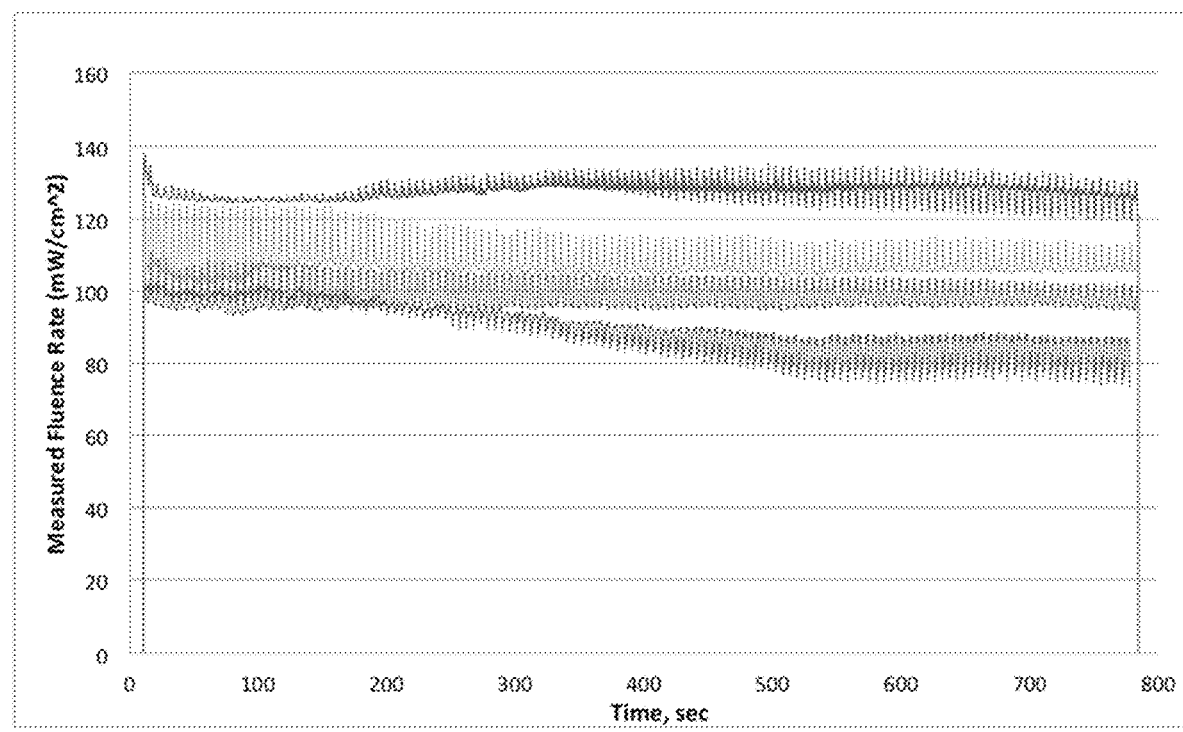
FIG. 7 is a graph showing the result of in vivo testing in the chest of an adult pig, showing the achievement of relatively uniform light distribution.

In a test configuration shown in FIG. 5, Lewis Lung Carcinoma (LLC) cells were seeded into 96-well culture dishes. When cells reached approximately 95% confluence Photofrin was added at 0, 1, 2, 3, 10, and 30 µg/mL. Cells were incubated at 37° C. in the dark for ~24 hours. Media was removed and fresh media added. Immediately after the dishes were positioned over the center of the PDT surface applicator with a layer of ballistic gel tissue phantom between the flap and the culture dish. Two 3 cm long diffusing fibers were placed 6 cm apart in the flap. LLC cells were exposed topo 1.5 J/cm$^2$ 630 nm light from a laser diode. PDT effect was determined 24 hours later using an MTT assay. Results are shown in FIG. 6.

Figure 8:
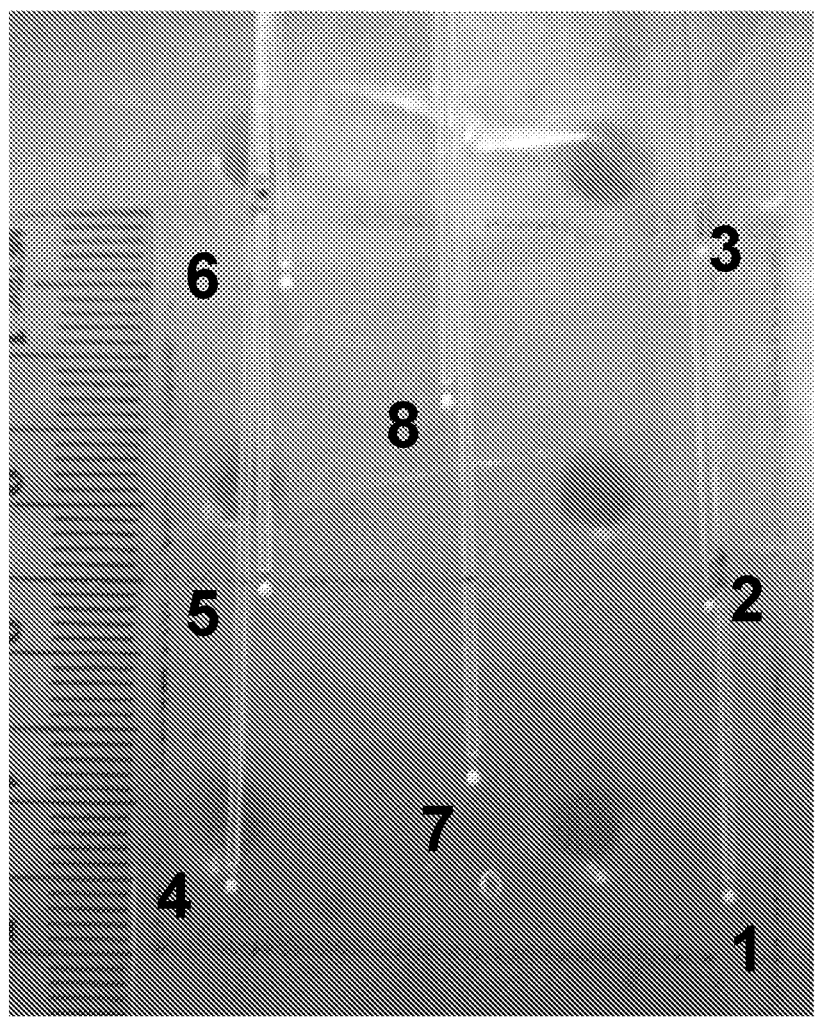
FIG. 8 shows a test detection area using 8 fibers in a 4×5 cm area.
Figure 9:
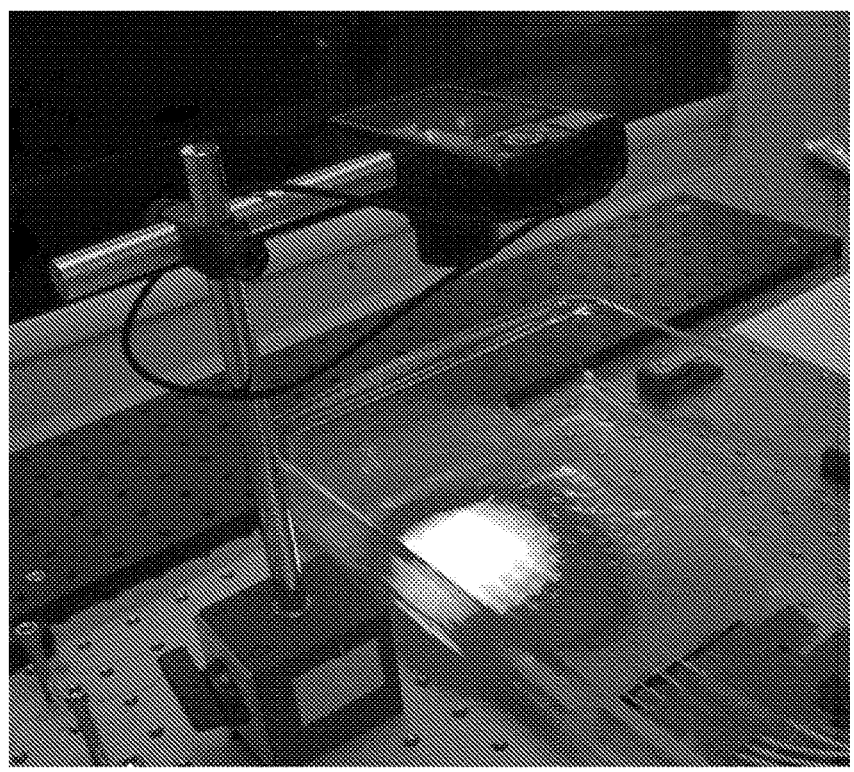
FIG. 9 shows the test configuration of FIG. 8 in a flap, shown under test.
Figure 10:
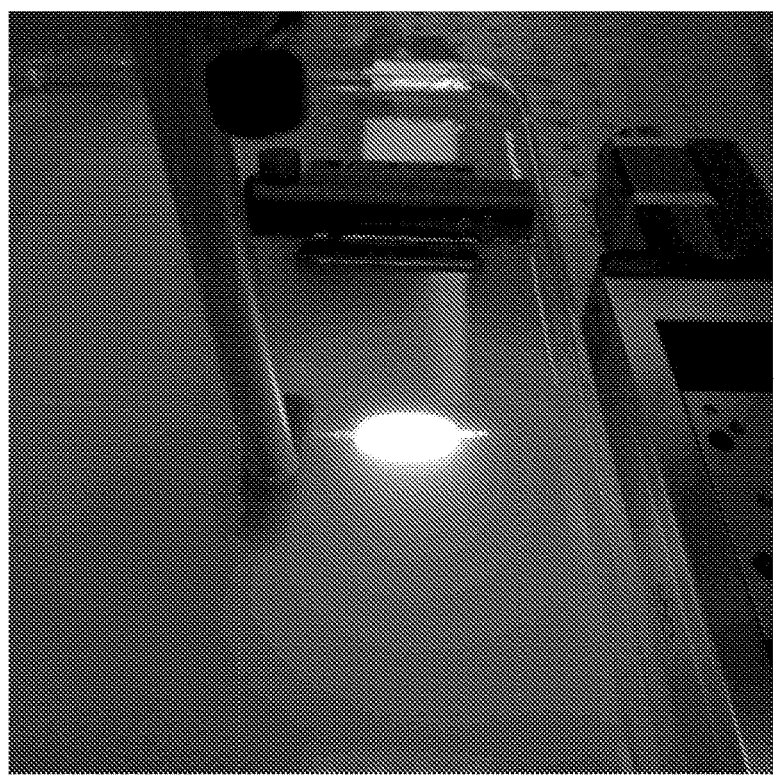
FIG. 10 shows a comparison configuration using a balloon, shown under test.
Figure 11:
FIG. 11 shows the flap configuration of FIG. 9 with gold foil.
Figure 12:
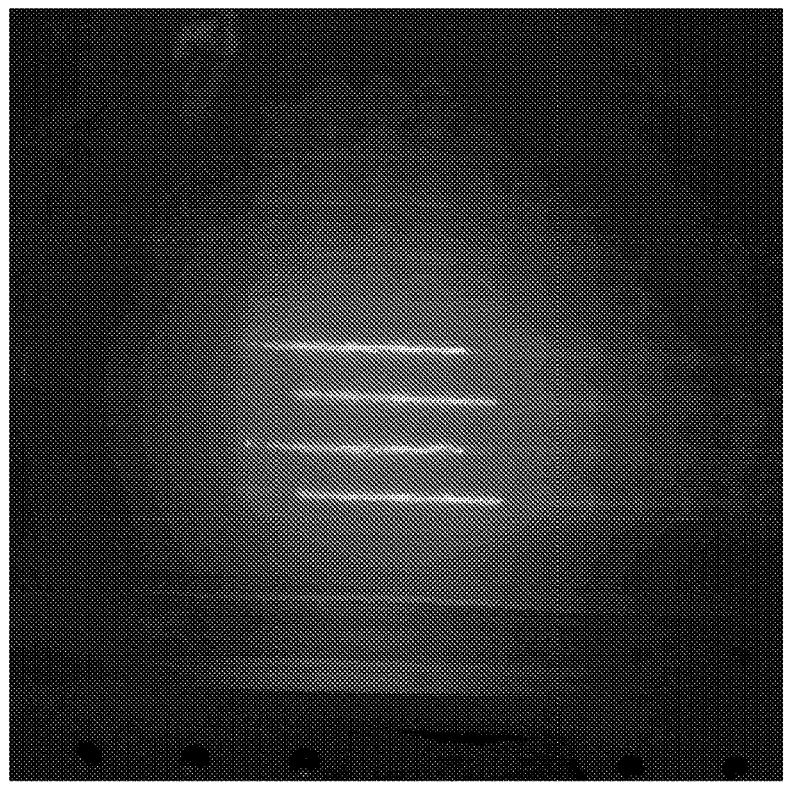
FIG. 12 shows the flap configuration of FIG. 9 without gold foil.

Tests comparing the presently-disclosed flap device with a balloon device were performed using air, water, or 0.01% intralipid media. The tests incorporated a 4×5 cm detection area, IP-85 probes between 2 gel layers, and 400 mW of light at a wavelength 652 nm. FIG. 8 shows 8 fibers used in the 4×5 cm area with 3 fibers along two edges and 2 fibers in the middle. A 10×10 cm flap was used with 1-4 cylindrical fibers (see FIG. 9). The flap was tested with gold foil (FIG. 11) and without (FIG. 12). In comparison, a 3 cm balloon was used with a single cylindrical fiber delivering a total of 400 mW (FIG. 10). The scans were performed at 1 mm/s, with 0.05 mm steps, at 0.3 cm from the phantom surface. Data was acquired over 50 seconds. Results for both configurations are shown in FIG. 13.

Although the present disclosure has been described with respect to one or more particular embodiments, it will be understood that other embodiments of the present disclosure may be made without departing from the spirit and scope of the present disclosure. Hence, the present disclosure is deemed limited only by the appended claims and the reasonable interpretation thereof.

We claim:

1. A method for light therapy of a tissue surface, comprising:
    placing an articulating guide onto the tissue surface such that the guide conforms to the surface such that a plurality of channels of the guide are spaced apart a same distance from the tissue surface over a length of each channel of the plurality of channels;
    inserting a treatment fiber axially into a first channel of the plurality of channels of the articulating guide until a working end of the treatment fiber reaches a first location along the length of the first channel;
    coupling an external light source to the treatment fiber;
    causing a light to be transmitted through the treatment fiber and to emit from the working end of the treatment fiber; and
    moving the treatment fiber axially in the first channel during the light therapy until the working end of the treatment fiber reaches a second location along the length of the first channel.

2. The method of claim 1, wherein more than one treatment fiber is inserted, each treatment fiber being inserted into a corresponding channel of the plurality of channels of the articulating guide.

3. The method of claim 2, wherein each treatment fiber is moved together with the other treatment fibers.

4. The method of claim 2, wherein at least one of the more than one treatment fibers is moved independently of another treatment fiber.

5. The method of claim 1, wherein the treatment fiber is alternately moved between the second location and the first location until a sufficient light dose has been received by the tissue surface.

6. The method of claim 1, further comprising measuring a light dose of a location of the tissue surface.

7. The method of claim 6, further comprising inserting a dosimetry fiber into a channel of the plurality of channels of the articulating guide.

8. The method of claim 1, further comprising securing the articulating guide onto the tissue surface.

9. The method of claim 8, wherein the articulating guide is secured to the tissue surface by way of suturing.

10. The method of claim 1, wherein the treatment fiber is moved at a speed corresponding to a desired light dosage rate.

11. The method of claim 1, further comprising varying an intensity of the light.

12. The method of claim 1, wherein the light comprises more than one wavelength.

13. A system for light therapy of a tissue surface, comprising:
    an articulating guide having a plurality of channels each having a length, the articulating guide configured to conform to the tissue surface such that the plurality of channels are substantially a same distance from the tissue surface over the length of the plurality of channels;
    a treatment fiber having a length and having a working end configured to emit light, the treatment fiber-configured to be movably disposed axially along the length of a channel of the plurality of channels; and
    an external light source in light-transmitting communication with the treatment fiber configured to transmit light along the length and to emit light from the working end of the treatment fiber.

14. The system of claim 13, wherein the articulating guide comprises a plurality of spheres having a passage therethrough, the plurality of spheres disposed in one or more rows, wherein the passages of each sphere of a row are aligned to form a channel.

15. The system of claim 14, wherein the plurality of spheres are translucent.

16. The system of claim 15, wherein the plurality of spheres are made from silicone rubber.

17. The system of claim 14, wherein the plurality of spheres are each 1 cm in diameter.

18. The system of claim 14, wherein the passage of each sphere passes through a diameter of the sphere.

19. The system of claim 13, further comprising a sheet disposed between the articulating guide and the tissue surface.

20. The system of claim 13, wherein a sheet is disposed on a side of the articulating guide opposite the tissue surface.

21. The system of claim 13, further comprising a microprocessor in operable communication with the light source and configured to control an intensity of the light source.

22. The system of claim 13, further comprising an armature configured to move the treatment fiber within the channel.

\* \* \* \* \*